(12) United States Patent
Veronique et al.

(10) Patent No.: US 6,512,111 B1
(45) Date of Patent: Jan. 28, 2003

(54) PROCESS FOR THE PREPARATION OF BICYCLIC COMPOUNDS AND THE USE OF THIS PROCESS FOR THE PREPARATION OF AN ICE INHIBITOR COMPOUND

(75) Inventors: Crocq Veronique, Dijon (FR); Patrick Roussel, Thiais (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/869,950
(22) PCT Filed: Jan. 11, 2000
(86) PCT No.: PCT/FR00/00041
§ 371 (c)(1),
(2), (4) Date: Jul. 27, 2001
(87) PCT Pub. No.: WO00/42061
PCT Pub. Date: Jul. 20, 2000

(30) Foreign Application Priority Data

Jan. 12, 1999 (FR) .............................. 99 00227

(51) Int. Cl.[7] .............................. C07D 237/04
(52) U.S. Cl. ...................... 540/500; 544/224
(58) Field of Search .................. 540/500; 544/224

(56) References Cited

FOREIGN PATENT DOCUMENTS

EP          0094095          11/1983

OTHER PUBLICATIONS

Attwood et al, "The Design . . . Bicyclic Compounds", Journal of the Chemical Society, Perkin Transactions 1, Jan. 1, 1986, pp. 1011–1019.

Attwood et al, "New Potent . . . Converting Enzyme" Febs Letters, vol. 165, No. 2, Jan. 1, 1984, pp. 201–206.

*Primary Examiner*—Bruck Kifle
(74) *Attorney, Agent, or Firm*—Bierman, Muserlian and Lucas

(57) ABSTRACT

A method for preparing compounds of formula (I)

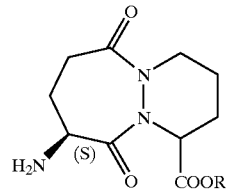

wherein R is selected from the group consisting of H. alkyl, aryl, and aralkyl of up to 18 carbon atoms and the amine function may be free or protected from a compound of formula (IA) wherein cyclization is carried out in a basic medium and in the presence of a phosphonic acid derivative and the use of said method as an intermediate step for preparing a compound inhibiting the interleukin-1 beta conversion enzyme.

13 Claims, No Drawings

PROCESS FOR THE PREPARATION OF BICYCLIC COMPOUNDS AND THE USE OF THIS PROCESS FOR THE PREPARATION OF AN ICE INHIBITOR COMPOUND

This application is a 371 of PCT/FR00/00041 filed Jan. 11, 2000.

A subject of the present invention is a novel process for the preparation of bicyclic compounds and the use of this process as an intermediate stage in the preparation of a compound which inhibits the interleukin-1 beta converting enzyme (ICE).

The compound of formula (I) as defined below, in which R represents a terbutyl radical and the amine is protected in the form of phthalimido, is described in the Patent EP 94095. This compound of formula (I) is also used for the preparation of the compound of formula (V) having an inhibitory activity on the interleukin-1 beta converting enzyme described in the International Application WO 97/22619.

One of the objectives of the invention is to find a novel process of obtaining the compounds of formula (I).

Therefore a subject of the invention is a process for the preparation of the compounds of formula (I)

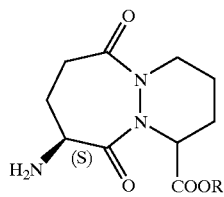

(I)

in which R represents a hydrogen atom, an alkyl, aryl or aralkyl radical containing up to 18 carbon atoms and the amine function can be free or protected, starting from a compound of formula (IA)

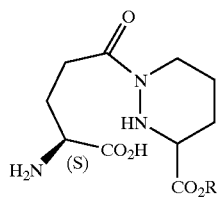

(IA)

in which R has the same meaning as previously and the amine function can be free or protected, characterized in that the cyclization is carried out in a basic medium and in the presence:

of a derivative of phosphonic acid of formula (P1):

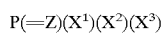

in which Z is a sulphur or oxygen atom, $X^1$ represents a halogen atom, $X^2$ and $X^3$, identical or different, represent a halogen atom, an alkyloxy radical containing 1 to 6 carbon atoms, an aryloxy radical containing 6 to 12 carbon atoms or an arylalkyloxy radical containing 7 to 15 carbon atoms, or of a trimer of formula (P2)

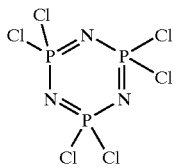

R preferably represents a hydrogen atom, a methyl, ethyl, propyl, isopropyl, n-butyl, isobutyl, tertbutyl, benzyl, phenyl or naphthyl radical and quite particularly methyl, ethyl and tertbutyl.

When the amine function is protected, the protection can be done according to the standard methods known to a person skilled in the art.

The amine function can be protected in the form of an $-NR^1R^2$ radical in which
either $R^1$ represents a

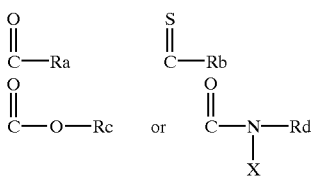

radical, Ra, Rb, Rc and Rd representing an alkyl or aryl radical containing up to 18 carbon atoms or a mono or polycyclic radical containing one or more heteroatoms, X representing a hydrogen atom, an alkyl radical containing up to 8 carbon atoms or an aryl radical containing up to 14 carbon atoms, and $R^2$ represents a hydrogen atom,
or $R^1$ and $R^2$ together form a mono or polycyclic radical containing 1 or more heteroatoms. The amine can thus be protected in the form of a phthalimido

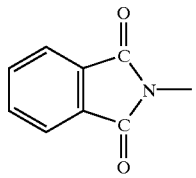

or also in the form of the

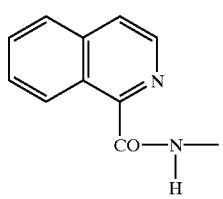

radical.

Preferably, the amine is protected in the form of a phthalimido.

Among the derivatives of phosphonic acid of formula $P(=Z)(X^1)(X^2)(X^3)$, it is in particular the following derivatives:

(Cl)P(O)(Ph)$_2$, (Cl)$_2$P(O)(OPh)$_2$, (Cl)P(O)(OEt)$_2$, (Cl)$_2$P(O)(OEt)$_2$, POCl$_3$, POBr$_3$ and P(S)Cl$_3$.

The cyclization reaction is preferably carried out in the presence of POCl$_3$ or POBr$_3$ and the base is in particular an organic base, for example triethylamine, pyridine or 2,6-lutidine.

A more particular subject of the invention is the process as described previously in which the trihalogenophosphonic acid is POCl₃.

A more particular subject of the invention is the process as described previously in which the trihalogenophosphonic acid is POBr₃.

A more particular subject of the invention is the process as described previously in which the base is chosen from pyridine or 2,6-lutidine.

A more particular subject of the invention is the process as defined previously characterized in that the cyclization temperature is comprised between 70 and 80° C.

A more particular subject of the invention is the process as defined previously characterized in that the solvent is dichloroethane.

The compound of formula (IA) is in the form of a mixture of SS and SR diastereoisomers or in the form of the SR diastereoisomer.

The compound of formula (I) is in the form of a mixture of SS and SR diastereoisomers or in the form of the SR diastereoisomer.

A subject of the invention is also a process for the preparation of the compound of formula (I) in racemic or optically active (Iopt) form, comprising the cyclization process as described above, and characterized in that it comprises the following successive stages:

a) A compound of formula (II)

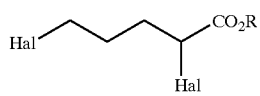

(II)

in which R is as defined previously and Hal represents a halogen atom, is subjected to the action of a compound of formula (III)

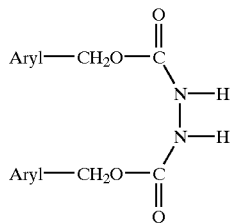

(III)

in which Aryl represents an aryl radical containing up to 14 carbon atoms, in order to obtain the compound of formula (IV)

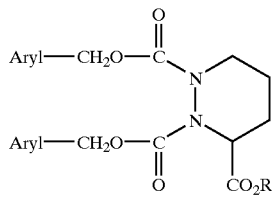

(IV)

in the form of a mixture of S and R stereoisomers, b) the compound of formula (IV) is subjected to the action of an anhydride of formula (F)

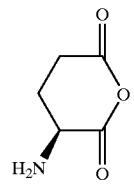

(F)

the amine function being in protected or non-protected form, while carrying out a deprotection by hydrogenolysis, in order to obtain the compound of formula (IA)

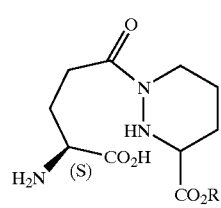

(IA)

as defined above, c) the compound of formula (IA) is subjected to the action of a derivative of phosphonic acid (P1) or (P2) as defined above, in the presence of a base, in order to obtain the compound of formula (I) as defined above

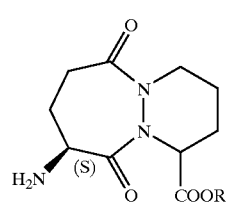

(I)

d) if appropriate, the amine function is deprotected in order to obtain the compound of formula (I) in which the amine function is not protected, e) if appropriate, the compound of formula (I) in the SS+SR or SR form is subjected to the action of a deracemization and/or epimerization agent in order to obtain the compound of formula (Iopt) corresponding to the SS diastereoisomer,

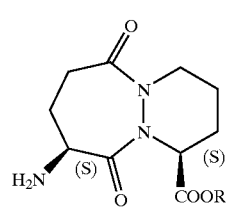

(Iopt)

f) if appropriate, the amine function is deprotected in order to obtain the compound of formula (Iopt) in which the amine function is not protected.

In a preferred embodiment:

Hal represents a chlorine atom;

R represents an alkyl radical containing 1 to 4 carbon atoms;

Aryl represents a phenyl or naphthyl radical,

Compound (F) is N-phthaloyl-L-glutamic anhydride

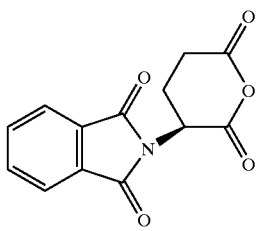

The amine function of the compounds of formulae (IA), (I) or (Iopt) is in protected form and in particular in phthalimido form;

The reaction between the compounds of formula (II) and the compounds of formula (III) takes place in the presence of a base for example in the presence of an alkaline carbonate such as potassium carbonate;

The deprotection by hydrogenolysis is carried out according to standard conditions known to a person skilled in the art, for example the hydrogenolysis agent is hydrogen in the presence of palladium on carbon;

The deracemization and/or epimerization agent is a base, more especially a strong base, for example an alkaline or alkaline-earth alcoholate such as sodium or potassium methylate, sodium or potassium terbutylate or a lithiated amine such as LDA;

The action of a deprotection agent of the amine can be carried out in particular by the action of a hydrazine.

A quite particular subject of the invention is the process as defined previously in which (F) is the anhydride of phthaloyl glutamic acid.

A quite particular subject of the invention is the process as defined previously in which the amine function of the compounds of formulae (IA), (I) or (Iopt) is protected in the form of a phthalimido group.

A quite particular subject of the invention is the process as defined previously in which, within the compounds of formula (II), (IV), (IA), (I) and (Iopt), R is a methyl, ethyl or tertbutyl radical.

A quite particular subject of the invention is the process as defined previously in which the compound of formula (I) is ethyl 9-(1,3-dihydro-1,3-dioxo-2H-isoindol-2-yl)-3,4,7,8, 9,10-hexahydro-6,10-dioxo-6H-pyridazino-[1,2-a][1,2] diazepine-1-carboxylate:

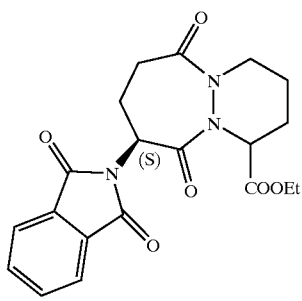

A quite particular subject of the invention is the process as defined previously in which the compound of formula (Iopt) is ethyl-(1S-cis)-9-(1,3-dihydro-1,3-dioxo-2H-isoindol-2-yl)-3,4,7,8,9,10-hexahydro-6,10-dioxo-6H-pyridazino-[1,2-a][1,2]diazepine-1-carboxylate:

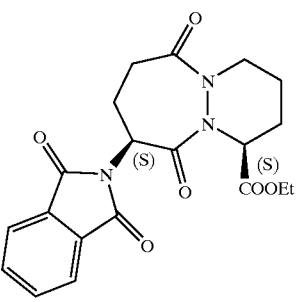

The compounds of formula (I) can in general be used for the synthesis of medicaments as indicated in the Patent EP 94095. The compounds of formulae (II) and (III) and (F) are known and can be prepared according to the experimental method described below.

A subject of the invention is also the use of the process as defined above as an intermediary stage for the preparation of a compound of formula (V)

(V)

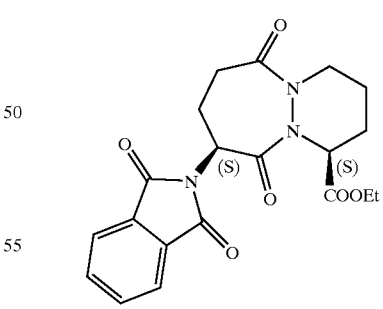

via the compound of formula (Iopt) as defined previously, characterized in that this process comprises the stages of the process for the preparation of the compounds of formula (Iopt) starting from the compounds of formula (II) as defined previously.

A subject of the invention is also the use as defined above, characterized in that the compound of formula (Iopt) is ethyl (1S-cis)-9-(1,3-dihydro-1,3-dioxo-2H-isoindol-2yl)-3,4,7,8, 9,10-hexahydro-6,10-dioxo-6H-pyridazino-[1,2-a][1,2] diazepine-1-carboxylate

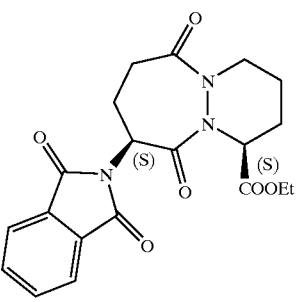

A subject of the invention is also the use of the process as defined above as an intermediate stage of the overall preparation process for the compounds of formula (I) and (Iopt) as defined previously.

Finally, a subject of the invention, as an intermediate compound, is the compound of formula (IA) as defined previously.

The following examples illustrate the invention without however limiting it.

Preparation 1

Preparation of bis(phenylmethyl) 1,2-hydrazinecarboxylate 1.5 liters of methanol and 25 g of hydrazine monohydrate at 80% are placed under nitrogen. The reaction medium is cooled down to 0° C. and then 75 g of benzyl chloroformate and a solution of 93 g of sodium carbonate in 1100 ml of demineralized water are introduced. The reaction mixture is maintained at 0° C. for 1 hour, followed by separating and washing by displacement with a mixture of 100 ml of methanol and 100 ml of water, then washing by displacement with 500 ml of water at 0° C. After drying 107.6 g of sought product is obtained.

Preparation 2

Preparation of N-phthaloyl-L-glutamic Anhydride D (+)
2-tetrahydro-2,6-dioxo-2H-pyran-3-yl-1H-isoindole-1,3(2H)-dione (R)

Stage a: N-phthaloyl-L-glutamic Acid 2-(1,3-dihydro-1,3-dioxo-2H-isoindole-2-yl)-pentanedioic acid (2S)

10 g of L-glutamic acid then 16 g of N-carbethoxyphthalimide (Nefkens reagent, commercial) are added to a solution of 14.4 g of sodium carbonate in 180 ml of water. Agitation is carried out at ambient temperature for 2 hours followed by extraction with ethyl acetate. The organic phase is evaporated under reduced pressure until a dry extract is obtained and 2.74 g of crude product is obtained. Washing is carried out with sodium bicarbonate, then after returning to the acid and extraction with ethyl acetate, 370 mg of expected product and $H_2N—CO_2Et$ are isolated. Moreover, the aqueous phase is adjusted to pH=2 with 36% hydrochloric acid at a temperature lower than 5° C. then extracted with ethyl acetate, washed with a saturated solution of sodium chloride, dried, filtered and concentrated under reduced pressure until 22.7 g of expected product is obtained in the form of an oil.

Mass spectrum $(M-H)^-=276^-$

Infrared (Nujol): 1775 $cm^{-1}$(m), 1720 $cm^{-1}$ (F, complex): CO 1611 $cm^{-1}$: Aromatic Stage b:

160 ml of tetrahydrofuran is added and 18.6 g of DCC (1,3-Dicyclohexyl-carbodiimide) in solution in 55 ml of tetrahydrofuran is added dropwise over 30 minutes to the product obtained in stage a). Agitation is carried out for 1 hour at 15–17° C., followed by filtering, rinsing with tetrahydrofuran, evaporating under reduced pressure until a dry extract is obtained which is taken up in isopropyl oxide. After agitation for 30 minutes, filtering is carried out followed by washing and drying. 14.98 g of expected product is obtained.

$\alpha_D=-52.63$ $^1H$ NMR (DMSO) 2.12 (m, 1H); 2.61 (m, 1H); 2.98 (dm, 1H); 3.16 (ddd, 1H); 5.48 (dd, 1H); 7.82 (m, >4H)

EXAMPLE 1

Ethyl (1S-cis)-9-(1,3-dihydro-1,3-dioxo-2H-isoindol-2-yl)-3,4,7,8,9,10-hexahydro-6,10-dioxo-6H-pyridazino-[1,2-a][1,2]diazepine-1-carboxylate Stage a: Preparation of 2,5-dibromopentanoic Acid 39 ml of bromine is added to a mixture of 106 g of 5-bromopentanoic acid and 1 ml of phosphorus tribromide. The reaction mixture is taken to 70–80° C. for 16 hours 30 minutes. The reaction medium is taken to 100° C. for 15 minutes and allowed to return to ambient temperature. 147 g of sought product is obtained.

Stage b: Preparation of Ethyl 2,5-dibromopentanoate 24.37 g of oxalyl chloride is added to a mixture containing 50 g of the acid prepared in the previous stage, 15 drops of dimethylformamide and 300 ml of dichloromethane. The reaction mixture is maintained under agitation, at ambient temperature, until the reaction is complete. The reaction mixture is cooled down to 10° C. and 50 ml of ethyl alcohol is added. Agitation is carried out for 30 minutes at 10° C., the reaction medium is left to return to ambient temperature and agitation is carried out for 3 hours at ambient temperature, followed by bringing to dryness and the sought product is obtained.

Stage c: Cyclization

Preparation of 3-ethyl-1,2-bis(phenylmethyl) (S)-tetrahydro-1,2,3-pyridazinetricarboxylate and 3-ethyl-1,2-bis(phenylmethyl) (R)-tetrahydro-1,2,3-pyridazine-tricarboxylate A suspension of 12.1 g of ethyl 2,5-dibromopentanoate (Stage b) in 50 ml of diglyme is introduced at 20–25° C. into a suspension containing 10.42 g of bis(phenylmethyl) 1,2-hydrazine-carboxylate (Preparation 1), 65 ml of diglyme and 8.26 g of potassium carbonate. The suspension obtained is heated at 90° C. and agitation is maintained for 48 hours, followed by cooling down to 20° C., pouring into a solution containing 50 ml of 2N hydrochloric acid and 150 ml of a mixture of water and ice. Extraction is carried out with ethyl acetate, followed by washing with water, drying, filtering, rinsing with ethyl acetate and drying. Finally, the crude product is purified by chromatography on silica eluting with a heptane/ethyl acetate mixture 40/20 and 10.71 g of sought product is obtained.

Stage d: Acylation and Hydrogenolysis

Preparation of (1S)-[3-oxo-3-(tetrahydro-3-ethoxycarbonyl-1(2H)-pyridazinyl)propyl]-1,3-dihydro-1,3-dioxo-2H-isoindole-2-acetic Acid α, The mixture constituted by 15 g of 3-ethyl-1,2-bis(phenylmethyl)tetrahydro-1,2,3-pyridazinetricarboxylate in the form of an R+S mixture as prepared in Stage c, 150 ml of tetrahydrofuran, 2.5 g of palladium on carbon (10%) and 9.08 g of phthaloyl glutamic acid anhydride as prepared according to Preparation 2 is placed under hydrogen pressure (1.3 bar) for 24 hours. After filtration, evaporation under reduced pressure is carried out until a dry extract is obtained which is taken up in 100 ml of ethyl acetate and 150 ml of a saturated solution of sodium bicarbonate. Extraction is carried out 3 times and the bicarbonate solution is acidified to pH=3 with 36% hydrochloric acid. Extraction is carried out 3 times with dichloromethane followed by washing with water. 13.16 g of crude product is obtained which is purified by chromatography on silica eluting with a toluene/ethyl acetate/acetic acid mixture 20/80/1.5 in order to obtain 12.7 g of expected product.

NMR (250 Hz, $CDCl_3$): 1.24 (d, 3H, $OCH_2C\underline{H}_3$); 4.12 (q, 2H, $OC\underline{H}_2CH_3$); 4.36–4.40 (m, 1H, H1 in position alpha or beta); 4.69–4.92 (m, 1H, H9 in position alpha); 7.70–7.86 aromatic H's.

Stage e1: Cyclization with $POCl_3$
ethyl-(1S-cis)-9-(1,3-dihydro-1,3-dioxo-2H-isoindol-2-yl)-3,4,7,8,9,10-hexahydro-6,10-dioxo-6H-pyridazino-[1,2-a][1,2]diazepine-1-carboxylate.
ethyl -(1R-trans)-9-(1,3-dihydro-1,3-dioxo-2H-isoindol-2-yl)-3,4,7,8,9,10-hexahydro-6,10-dioxo-6H-pyridazino-[1,2-a][1,2]diazepine-1-carboxylate.

The following solutions A and B:

A: 417 mg of the ester prepared in Stage d in 4 ml of dichloroethane to which 1 ml of a solution of 1.2 ml of 2,6-lutidine in 5 ml of dichloroethane has been added.

B: 1 ml of a solution of 1.9 ml of POCl₃ in 10 ml of dichloroethane, are added over 3 hours and simultaneously to a solution of 20 ml of dichloroethane heated beforehand to 75° C., then agitation is carried out for 1 hour at this temperature. The reaction medium is cooled down to 10° C., demineralized water is added, followed by extraction with dichloromethane and evaporation under reduced pressure in order to obtain a crude product (0.415 g) which is purified by chromatography on silica eluting with a heptane/dichloromethane-/ethyl acetate mixture 1/1/1. 161.8 mg of the SS diastereoisomer, 126.7 mg of the SR diastereoisomer and 5.8 mg of an SS+SR mixture are isolated.

Stage e2: Cyclization with POBr₃
ethyl-(1S-cis)-9-(1,3-dihydro-1,3-dioxo-2H-isoindol-2-yl)-3,4,7,8,9,10-hexahydro-6,10-dioxo-6H-pyridazino-[1,2-a][1,2]diazepine-1-carboxylate.
ethyl-(1R-trans)-9-(1,3-dihydro-1,3-dioxo-2H-isoindol-2-yl)-3,4,7,8,9,10-hexahydro-6,10-dioxo-6H-pyridazino-[1,2-a][1,2]diazepine-1-carboxylate.

The following solutions A and B:
A: 417 mg of the ester prepared in Stage d in 4 ml of dichloroethane to which 1 ml of a solution of 2.4 ml of 2,6-lutidine in 10 ml of dichloroethane has been added.
B: 1 ml of a solution of 5.85 g of POBr₃ in 10 ml of dichloroethane, are added over 3 hours and simultaneously to a solution of 20 ml of dichloroethane heated beforehand to 80° C., then agitation is carried out for 1 hour to this temperature. The reaction medium is cooled down 10° C., demineralized water is added, followed by extraction with dichloromethane and evaporation under reduced pressure in order to obtain a crude product (0.419 g) which is purified by chromatography on silica eluting with a heptane/dichloromethane/ethyl acetate mixture 1/1/1. 163 mg of the SS diastereoisomer, 143 mg of the SR diastereoisomer and 6.2 mg of an SS+SR mixture are isolated.

Stage f: Deracemization/epimerization
ethyl-(1S-cis)-9-(1,3-dihydro-1,3-dioxo-2H-isoindol-2-yl)-3,4,7,8,9,10-hexahydro-6,10-dioxo-6H-pyridazino-[1,2-a][1,2]diazepine-1-carboxylate.

A solution containing 0.029 g of potassium terbutylate and 0.3 ml of dimethylformamide is introduced at a temperature of −45/−48° C. over one hour 30 minutes into a mixture containing 0.194 g of the SS+SR mixture prepared in Stage d, 1.5 ml of dimethylformamide and 0.75 ml of terbutanol. The mixture is maintained under agitation for 1 hour and after cooling down to −50° C., 0.4 g of ammonium chloride in powder form is introduced. Agitation is carried out for 10 minutes at −45° C., 1 ml of ammonium chloride is added at 20° C. and agitation is carried out again for 10 minutes. After 5 minutes, 2 ml of demineralized water is added, followed by extraction with ethyl acetate, washing with demineralized water, decanting, concentrating and drying. 0.166 g of the expected SS diastereoisomer is obtained.

$\alpha_d = -75.3°$ (1% in methanol)

NMR (250 Hz, CDCl₃): 1.73 (m, 3H, H-2alpha H-3alpha H-3beta; 1.24 (d, 3H, OCH₂CH₃); 2.38 (m, 3H, H2beta, H7alpha, H8alpha); 2.92 (m, 1H, H4alpha); 3.39–3.44 (m, 1H, H8beta); 3.62(m, 1H, H7beta); 4.23 (m, 2H, OCH₂CH₃); 4.66–4.71 (m, 1H, H4 in position beta); 5.26–5.41 (m, 2H, H1 and H9 in position alpha); 7.72–7.88 aromatic H's.

What is claimed is:
1. A process for the preparation of a compound of the formula

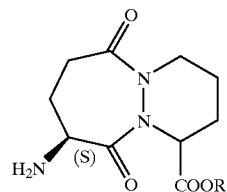

(I)

wherein R is selected from the group consisting of hydrogen, and alkyl, aryl and aralkyl up to 18 carbon atoms and the amine function can be free or protected comprising cyclizing a compound of the formula

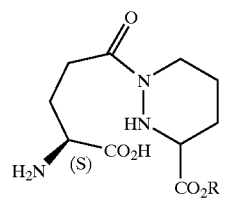

(IA)

wherein R has the above meaning and the amine function can be free or protected in a basic medium and in the presence:

of a derivative of phosphonic acid of the formula $P(=Z)(X^1)(X^2)(X^3)$  P₁ wherein Z is a sulfur or oxygen, $X^1$ is halogen, $X^2$ and $X^3$ are individually selected from the group consisting of halogen, alkoxy, of 1 to 6 carbon atoms, aryloxy of 6 to 12 carbon atoms and arylalkoxy of 7 to 15 carbon atoms, or of a trimer of the formula

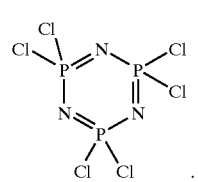

P₂

2. The process of claim 1 wherein (P1) is POCl₃.
3. The process of claim 1 wherein (P1) is POBr₃.
4. The process of claim 1 wherein the base is pyridine or 2,6-lutidine.
5. The process of claim 1 wherein the cyclization temperature is between 70 and 80° C.
6. The process of claim 1 wherein the solvent is dichloroethane.
7. A process for the preparation of a compound of formula (I) in racemic or optically active (Iopt) form, comprising
a) reacting a compound of the formula

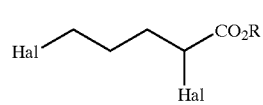

II wherein R is selected from the group consisting of hydrogen and alkyl, aryl and aralkyl of up to 18 carbon atoms and Hal is halogen with a compound of the formula

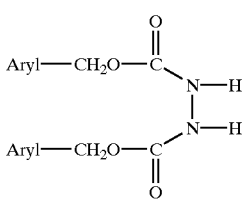

wherein Aryl is aryl of up to 14 carbon atoms, to obtain a compound of the formula

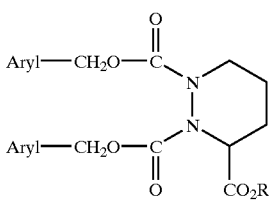

in the form of a mixture of R and S stereoisomers b) reacting a compound of formula (IV) with an anhydride of the formula

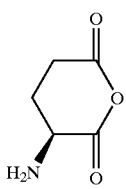

with the amine function being protected or non-protected while carrying out a deprotection by hydrogenolysis to obtain a compound of the formula

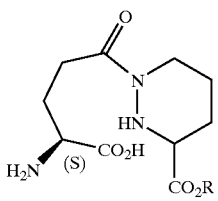

c) reacting a compound of formula (IA) with a derivative of phosphonic acid (P1) or (P2) of claim 1 in the presence of a base to obtain a compound of the formula

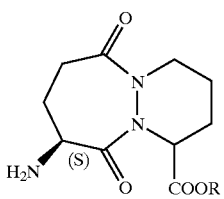

d) optionally, the amine function is deprotected to obtain a compound of formula (I) in which the amine function is not protected, e) optionally, the compound of formula (I) in the SS+SR or SR form is reacted with a deracemization and/or epimerization agent to obtain the compound of formula (Iopt) corresponding to the SS diastereoisomer,

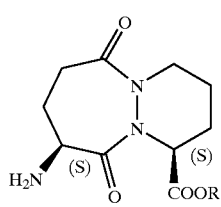

f) and optionally, the amine function is deprotected to obtain a compound of formula (Iopt) in which the amine function is not protected, g) The process of claim 7 wherein F is N-phthaloyl-L-glutamic anhydride of the formula

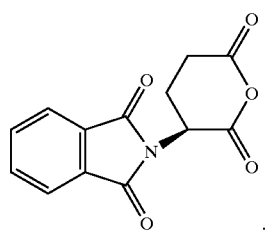

8. Process as defined in claim 7 in which F is N-phthaloyl-L-glutamic anhydride:

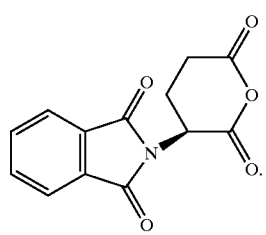

9. The process of claim 1 wherein the amine function of the compounds of formulae (IA), (I) and (Iopt) is protected in phthalimido form.

10. The process of claim 1 wherein R is methyl or ethyl or tertbutyl.

11. The process of claim 1 wherein the compound of formula (I) is ethyl-9-(1,3-dihydro-1,3-dioxo-2H-isoindol-2-yl)-3,4,7,8,9,10-hexahydro-6,10-dioxo-6H-pyridazino-[1,2-a][1,2]diazepine-1-carboxylate

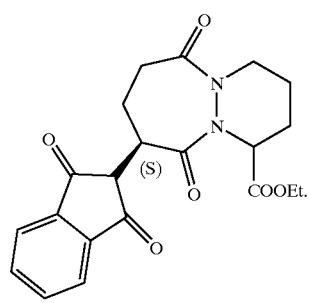

12. The process of claim 1 wherein the compound of formula (Iopt) is ethyl-(1S-cis)-9-(1,3-dihydro-1,3-dioxo- 2II isoindol-2-yl)-3,4,7,8,9,10-hexahydro-6,10-dioxo-6H-pyridazino-[1,2-a][1,2]diazepine-1-carboxylate:
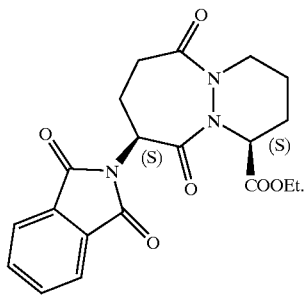
13. A compound of the formula
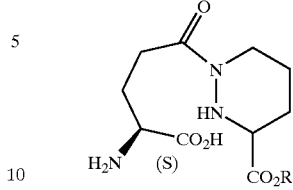
IA
wherein R is selected from the group consisting of hydrogen, alkyl of 1 to 18 carbon atoms and aryl and aralkyl of up to 18 carbon atoms and the amine group is free or protected.
* * * * *